US009465040B2

(12) United States Patent
Fuchs et al.

(10) Patent No.: US 9,465,040 B2
(45) Date of Patent: Oct. 11, 2016

(54) METHOD FOR PROFILING PHYTOHORMONE LEVELS IN PLANT TISSUE

(75) Inventors: Regine Fuchs, Berlin (DE); Martin Dostler, Henningsdorf (DE); Maria Wahl, Berlin (DE); Benjamin Hentschel, Berlin (DE); Ralf Looser, Berlin (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 310 days.

(21) Appl. No.: 14/111,369

(22) PCT Filed: Apr. 13, 2012

(86) PCT No.: PCT/IB2012/051818
§ 371 (c)(1),
(2), (4) Date: Dec. 23, 2013

(87) PCT Pub. No.: WO2012/140603
PCT Pub. Date: Oct. 18, 2012

(65) Prior Publication Data
US 2014/0147925 A1 May 29, 2014

Related U.S. Application Data

(60) Provisional application No. 61/475,709, filed on Apr. 15, 2011.

(30) Foreign Application Priority Data

Apr. 15, 2011 (EP) ..................................... 11162675

(51) Int. Cl.
*G01N 33/74* (2006.01)
*G01N 1/18* (2006.01)
*G01N 30/06* (2006.01)
*G01N 30/72* (2006.01)
G01N 30/00 (2006.01)
G01N 30/88 (2006.01)

(52) U.S. Cl.
CPC .............. *G01N 33/74* (2013.01); *G01N 30/06* (2013.01); *G01N 30/7233* (2013.01); *G01N 30/7266* (2013.01); *G01N 2030/009* (2013.01); *G01N 2030/062* (2013.01); *G01N 2030/8813* (2013.01); *Y10T 436/141111* (2015.01); *Y10T 436/145555* (2015.01); *Y10T 436/147777* (2015.01); *Y10T 436/201666* (2015.01); *Y10T 436/24* (2015.01); *Y10T 436/25* (2015.01); *Y10T 436/255* (2015.01); *Y10T 436/25125* (2015.01)

(58) Field of Classification Search
CPC .............. G01N 2030/009; G01N 2030/8813; G01N 30/00; G01N 30/02; G01N 30/04; G01N 30/06; G01N 30/7266; G01N 30/72; G01N 30/7233; G01N 33/74; Y10T 436/141111; Y10T 436/145555; Y10T 436/147777; Y10T 436/201666; Y10T 436/13; Y10T 436/24; Y10T 436/25; Y10T 436/25125; Y10T 436/25375; Y10T 436/255
USPC ......... 436/56, 161, 173, 174, 175, 177, 178, 436/129, 92, 96, 98; 422/68.1, 69, 70; 250/282; 210/656, 660, 661, 662, 210/198.2
See application file for complete search history.

(56) References Cited

PUBLICATIONS

Hoyerova et al. Phytochemistry, vol. 67, May 5, 2006, pp. 1151-1159.*
Kojima et al. Plant and Cell Physiology, vol. 50 (7), 2009, pp. 1201-1214.*
Birkemeyer et al., "Comprehensive Chemical Derivatization for Gas Chromatography-Mass Spectrometry-Based Multi-Targeted Profiling of the Major Phytohormones," Journal of Chromatography A, vol. 993, (2003), pp. 89-102.
Durgbanshi et al., "Simultaneous Determination of Multiple Phytohormones in Plant Extracts by Liquid Chromatography-Electrospray Tandem Mass Spectrometry," J. Agric. Food Chem., vol. 53, (2005), pp. 8437-8442.
Forcat et al., "A Rapid and Robust Method for Simultaneously Measuring Changes in the Phytohormones ABA, JA and SA in Plants Following Biotic and Abiotic Stress," Plant Methods, vol. 4, No. 16, (2008), pp. 1-8.
Hou et al., "Simultaneous Determination of Gibberellic Acid, Indole-3-Acetic Acid and Abscisic Acid in Wheat Extracts by Solid-Phase Extraction and Liquid Chromatography-Electrospray Tandem Mass Spectrometry," Talanta, vol. 76, (2008), pp. 798-802.
International Search Report, issued in PCT/IB2012/051818, dated Sep. 13, 2012.
Izumi et al., "Development of a Method for Comprehensive and Quantitative Analysis of Plant Hormones by Highly Sensitive Nanoflow Liquid Chromatography-Electrospray Ionization-Ion Trap Mass Spectrometry," Analytica Chimica Acta, vol. 648, (2009), pp. 215-225.
Kojima, "Characteristics of HPLC Columns and Mass Spectra of LC-MS for Phytohormone Analysis," JARQ, vol. 35, No. 3, (2001), pp. 149-154.
Liu et al., "Simultaneous Determination of Phytohormones in Plant Extracts using SPME and HPLC," Chromatographia, vol. 66, (2007), pp. 515-520.

(Continued)

*Primary Examiner* — Maureen Wallenhorst
(74) *Attorney, Agent, or Firm* — Marshall, Gerstein & Borun LLP

(57) ABSTRACT

The present invention provides a method for profiling phytohormone levels in plant tissue or tissue of other plastid containing organisms, i.e. a method for the simultaneous determination of a multitude of phytohormone levels in plant tissue or tissue of other plastid containing organisms.

16 Claims, No Drawings

(56) References Cited

PUBLICATIONS

Matsuda et al., "Quantification of Indole-3-Acetic Acid and Amino Acid Conjugates in Rice by Liquid Chromatography-Electrospray Ionization-Tandem Mass Spectrometry," Biosci. Biotechnol. Biochem., vol. 69, No. 4, (2005), pp. 778-783.

Novák et al., "Cytokinin Profiling in Plant Tissues using Ultra-Performance Liquid Chromatography-Electrospray Tandem Mass Spectrometry," Phytochemistry, vol. 69, (2008), pp. 2214-2224.

Pan and Wang, "Profiling of Plant Hormones by Mass Spectrometry," Journal of Chromatography B, vol. 877, (2009), pp. 2806-2813.

Written Opinion, issued in PCT/IB2012/051818, dated Sep. 13, 2012.

* cited by examiner

METHOD FOR PROFILING PHYTOHORMONE LEVELS IN PLANT TISSUE

This application is a National Stage application of International Application No. PCT/IB2012/051818, filed Apr. 13, 2012, which claims the benefit of U.S. Provisional Application No. 61/475,709, filed Apr. 15, 2011. This application also claims priority under 35 U.S.C. §119 to European Patent Application No. 11162675.0, filed Apr. 15, 2011.

The present invention relates to a method for profiling phytohormone levels in plant tissue, in particular in tissue from crop plants.

Phytohormones play a crucial role as signalling molecules in the regulation of almost all processes in the lifecycle and development of plastid organisms such as plants, e.g. in their growth, differentiation, metabolism and morphogenesis. They also play an important role in mediating host responses to various biotic and abiotic stresses such as pathogen challenge, insect herbivores, drought, cold and heat stress. On the basis of their structure and physiological function phytohormones are characterized into several major classes including auxins, cytokinins, abscisic acids, gibberellins, ethylene, jasmonates, salicylates, strigolactones and brassinosteroids.

While the role of each class of hormone is well understood, recent studies have elucidated that multiple plant hormones often mediate development and stress response by co-action (cross-talk). Hence, simultaneous determination of multiple phytohormone levels in plant tissue will not only give a better understanding of physiological processes but also will more reliably indicate the presence of certain stress in the plant. In particular, simultaneous determination of a multitude of phytohormone levels in plant tissue will allow to infer, whether a certain stress induced by genetic engineering is absent or present in the plant organism. Therefore, several methods for simultaneous determination of multiple phytohormone levels in plant tissue have been suggested, which include either gas chromatography (GC) coupled with mass spectrometry (MS), in particular electron impact ionization mass spectrometry (EI-MS) (see e.g. Birkemeyer Journal of Chromatography A (2003) pp. 993 89-102) or high performance liquid chromatography (HPLC), coupled with mass spectrometry (MS), in particular electrospray ionization mass spectrometry (ESI-MS) (see e.g. X. Pan, X. Wang, Journal of Chromatography B, 877 (2009), pp. 2806-2813).

There are several problems associated with simultaneous analysis of phytohormone levels in plant tissues, including their low concentrations in the plant tissue ($10^{-9}$ M to $10^{-6}$ M) and complexity of the plant matrices. Therefore, efficient extraction, separation and purification techniques are normally required in order to obtain a material which reliably allows simultaneous determination of a multitude of phytohormone levels.

A. Durgbanshi et al., J. Agric. Food Chem. 53 (2005), pp. 8437-8442 describe a method of simultaneous determination of multiple phytohormones in plant extracts by coupled liquid chromatography-electrospray tandem mass spectrometry. The plant extracts were prepared by extracting comminuted plant materials either with methanol water (80:20) or water containing acetic acid, then partitioning the extract between diethylether, evaporating the organic phase and reconstituting the residue in water methanol, which, after filtration over cellulose acetate, was directly injected into the HPLC. By this method, only a limited number of analytes can be detected.

H-T Liu et al., Chromatographia 2007, 66, pp. 515-520 describe a method for simultaneous determination of indole acetic acid, indole butyric acid, abscisic acid and 1-napthylacetic acid in xylem fluid including solid-phase microextraction followed by HPLC. By this method, only a limited number of analytes can be detected.

S. Forcat et al., Plant methods, 2008, 4:16, describe a method for simultaneously measuring changes in the phytohormones abscisic acid (ABA), jasmonic acid (JA) and salicylic acid (SA) by subjecting a single crude extract directly to LC/MS/MS. Although this method is mentioned to be robust it is limited to polar analytes which can be reliably extracted with methanolic NaOH, e.g. ABA, JA and SA.

O. Novak et al., Phytochemistry 69 (2008), pp. 2214-2224 describe a method for profiling of cytokinin levels in plant tissues using ultra-performance liquid chromatography coupled with electrospray tandem mass spectrometry. The plant material was purified by solid phase extraction followed by an immuno-affinity clean-up step and two fast chromatographic separations. Although the method works well for cytokinins it has disadvantages in the determination of other phytohormones and, hence, it is not particularly useful for determination of phytohormones other than cytokinins. Apart from that it is expensive and time consuming, due to the use of immuno-affinity clean-up and thus not particularly useful for a high-throughput sample analysis.

Y. Izumi et al. Analytica Chimica Acta 648 (2009), pp. 215-225 describe a method for quantitative analysis of plant hormones by highly sensitive nanoflow liquid chromatography-electrospray ionization-ion trap mass spectrometry. Prior to the analysis, the extracts of the plant material were dried and reconstituted in solvent and the reconstituted extracts were purified by solid phase extraction. Nanoflow methods are generally less robust and less useful for high-throughput sample analysis.

Kojima et al. Plant Cell Physiol. 50(7) (2009), pp. 1201-1214 describe a method for high-throughput analysis of plant hormones by MS-probe modification and ultra performance liquid chromatography-tandem mass spectrometry. Prior to the analysis, the extracts of the plant material were purified by solid phase extraction comprising a first extraction over a hydrophobic material and a second extraction over a cationic ion exchanger from which several eluates were taken and separately analysed, optionally after derivatization or treatment with APase. By this method, certain analytes are such as JA, ABA and Brassinosteroide can not be detected. Although, this method has been suggested for high-throughput sample analysis this method is rather complex and thus not particularly suitable for high-throughput sample analysis.

The methods of prior art either require a very complex work-up of the plant extracts and/or they are limited with regard to the analytes and/or they are not useful for high-throughput sample analysis.

Therefore, it is an object of the present invention to provide a method for profiling phytohormone levels in plant tissue, which can be easily carried out without the need for a complex purification of plant extracts and which allows screening of a multitude of probes in a short time frame.

This object is solved by the method as defined herein and in the claims.

The present invention thus provides a method for profiling phytohormone levels in plant tissue or tissue of other plastid containing organisms, i.e. a method for the simultaneous determination of a multitude of phytohormone levels in plant tissue or tissue of other plastid containing organisms, which method comprises the following steps:

i. extraction of particulate tissue material of the plastid containing organism, in particulate tissue material of plants, with a liquid extractant, which is a mixture of at least one water miscible neutral organic solvent having from 1 to 3 carbon atoms and 1 heteroatom selected from O and N with water containing from 0.1 to 5% by weight, based on the extractant, of at least one acid, whereby a first liquid extract is obtained;

ii. contacting the liquid extract obtained in step i. with a solid absorbent having a hydrophobically modified surface and removing the solid absorbent to obtain a second liquid extract;

iii. evaporating the solvent from the second extract and then re-dissolving the obtained residue in a solvent mixture of at least one water miscible neutral organic solvent having from 1 to 3 carbon atoms and 1 heteroatom selected from O and N with water containing from 0.1 to 5% by weight, based on the solvent mixture, of at least one acid to obtain a reconstituted extract;

iv. purification of the reconstituted extract by contacting it with a solid absorbent having a hydrophobically modified surface to obtain a purified reconstituted extract (eluate); and v. determining the relative concentrations of at least two, frequently at least 4, in particular at least 6, especially at least 8 or at least 10 phyto, e.g. from 2 to 60, frequently from 4 to 50, in particular from 6 to 45, especially from 8 to 40 or from 10 to 30 plant hormones (phytohormones) in the purified reconstituted extract obtained in step iv. by directly subjecting the purified reconstituted extract to an analyzing unit comprising a separation unit for separation the phytohormones and an analyzer for identifying the phytohormones which separation unit is coupled to the analyzer.

The method of the present invention allows to simultaneously determine phytohormone levels of multitude of phytohormones in plant tissue material or tissue material of other plastid containing organisms in a reliable and easy way, i.e. it allows to determine the level of at least 2, frequently at least 4, in particular at least 6, especially at least 8 or at least 10 phytohormones, e.g. from 2 to 60, frequently from 4 to 50, in particular from 6 to 45, especially from 8 to 40 or from 10 to 30 phytohormones in one sample of the plant material at the same time. The method of the invention does not require tedious work-up of the plant material but simply requires simple treatment of the plant material with a liquid extractant, contacting the extractant with a specific absorbent followed by separating off the absorbent from the extractant, reconstituting the extractant and purification of the extractant by contacting it again with a specific absorbent. Thereby, a material is obtained which can be directly subjected to the analyzing unit. A derivatization prior to analysis is not necessary.

According to step i. of the claimed invention, particulate tissue material of the plastid containing organism, in particulate tissue material of a plant or plant organism, is extracted with a liquid extractant.

The type of tissue material to be analyzed is of minor importance and tissue material of a plastid containing organism refers to tissue material of plants or other organisms containing plastids in any stage of maturity or development (including seeds), as well as any tissue or organs (plant parts) taken or derived from any such plastid organism. Tissue materials include, but are not limited to, leave, flag leaf, floral leave, sepal, petal, petiol, inflorescence, flower bud, flower, stamen, anther, filament, pollen, pistill, style, stigma, ovary, ovule, embryo sac, ovum, infructescences, fruit, ear, cob, kernel, seed, seed case, seed coat, endosperm, seedling, meristematic region, shoot apical meristem, root apical meristem, lateral meristem, stem, internode, node, branche, tiller, lateral bud, root, storage root, lateral root, plant tissue culture, liquid plant cell culture, callus tissue culture, anther culture, microspore culture, protoplast culture and the like.

The method of the invention is not limited to tissue material of particular plastid containing organisms (hereinafter also termed "plastid organisms"), such as plants, but may applied to any plastid organisms, including plants and plastid organisms different from plants. Plastid organisms include plants, in particular crop plants, lower plant organisms like mosses or liverworts or other organisms containing plastids such as algae and cyanobacteriae.

Particular examples of plants from which the tissue material can be taken, include crop plants such as almond, apple, asparagus, avocado, banana, brassica, barley, basil, bean, cabbage, canola, carrot, celery, cherry, citrus, coffee, corn (maize), coconut, cotton, cucumber, flax, grass, hop, lettuce, mint, onion, e.g. dry bulb onion, green onion, orange, oats, oil palms, peach, peanut, pea, pear, pecan, potato, prune, rice, rye, sorghum, soybean, spinach, strawberry, sugarbeet, sugarcane, summer squash, sunflower, starfruit, tea, triticale, tomato, walnut wheat and vine or perennial grass, such as ryegrass and fescue or forage crops such as alfalfa and clover. The method of the invention is also useful for profiling phytohormone levels in non-crop plants including *Arabidopsis thaliana* or lemnoideae such as lemna, wolfia or spirodela.

The method of the invention is also useful for profiling phytohormone levels in lower plant organisms like mosses such as *Physcomitrella patens* or liverworts such as *Marchantia polymorpha*. The method of the invention is also useful for profiling phytohormone levels in other organisms containing plastids such as algae selected from the group of the families Bacillariophyceae, Charophyceae, Chlorophyceae, Chrysophyceae, Craspedophyceae, Euglenophyceae, Prymnesiophyceae, Phaeophyceae, Dinophyceae, Rhodophyceae, Xanthophyceae, Prasinophyceae such as the species *Acetabularia mediterranea, Dunaliella salina, Dunaliella tertiolecta, Euglena gracilis, Chlorella vulgaris* or microorganisms such as cyanobacteriae, e.g. cyanobacteria *Synechococcus, Synechocystis, Anabaena* or Chlorococcus.

Preferred embodiments of the invention relate to the profiling of phytohormone levels in plant tissue material, e.g. plant tissue material taken from crop-plants, in particular from crop-plants selected from the group consisting of corn (maize), rice, soybean, wheat, canola, cotton, sugar cane, and sugar-beet. Other embodiments of the invention relate to the profiling of phytohormone levels in plant tissue material taken from non-crop-plants.

The sample of the plastid containing organism can be taken from any plastid organism or any part of the plastid organism, independently of its occurrence and at any stage of its life-cycle, e.g. during the vegetative or reproductive growth of the organism. For example tissue materials of plant organisms can be taken from plants grown at arbitrary locations, e.g. in a greenhouse, field or growth chamber. The plant can be grown e.g. on soil or in hydroponic systems. Sample can be taken from a plant during the vegetative or reproductive growth. If the sample of a plant organism is taken from a plant grown on a field, the field can be e.g. a test field, where plants are imposed to abiotic stress conditions in order to monitor the plant performance (phenotypic and on phytohormone level) or a normal field, where farmers grow plants to later harvest them. Plant tissue material can be sampled from plants of a breeding population, transgenic plant, mapping population (NIL—near isogenic lines; RIL—recombinant inbred lines), or from plant cells from liquid culture.

According to the invention, a particulate tissue material is extracted. Particulate tissue material means that the tissue material is present during extraction in the form of fine particles, in order to achieve an efficient extraction of the plant material. Preferably the particle size of the tissue material to be extracted does not exceed 1 mm. Here and below, the particle size which the tissue material does not exceeded has to be understood as the value that is exceeded by less than 10% by weight, in particular less than 5% by weight of the particles to be extracted. Frequently, the tissue material to be extracted has particle size of 800 μm or less, in particular 700 μm or less, and especially 600 μm or less, 550 μm or less, 500 μm or less, 450 μm or less, or 400 μm or less. The particle size given here is the maximum diameter of the particles, which at least 90% by weight of the particles do not exceed ($D_{90}$ value), which can be easily determined by sieving.

The particles of the tissue material to be subjected to the method of the invention may occur in the form of particles fulfilling the above requirements or it may be comminuted to a fine particle size. Comminution of the tissue material may be performed during extraction or as a separate step, prior to extraction. Comminution, also known as size reduction, is defined as the breakdown of matrices, in particular solids, into smaller particles. Expediently, comminution is carried out mechanically. Comminution may be carried out in a single comminution operation or in subsequent comminution steps. Comminution of the tissue material can be achieved by standard measures for particle size reduction as described in the art, e.g. the prior art cited in the introductory part.

Comminution is normally carried out on dry tissue material, e.g. tissue material which has been lyophilized or freeze dried, respectively. The water content of the dry tissue plant material prior to comminution is normally below 20% by weight, in particular not more than 10% by weight. Comminution may also be carried out on fresh tissue material, i.e. non-dried tissue material, e.g. tissue material which has been frozen. Preferentially, comminution of fresh tissue is carried out at low temperatures, e.g. below −80° C., for example at temperatures in the range from <−80° C. to −200° C., in particular by using liquid nitrogen.

According to a preferred embodiment, comminution is carried out at reduced temperature. Temperatures below 0° C. and preferably below −20° C. are suitable, e.g. temperatures in the range from 0 to −200° C. or in the range from −20 to −200° C. Reduced temperatures may allow for a more efficient size reduction in case the sample or the particulate material is rather semi-solid than solid and/or minimize the decomposition of the analytes of interest and/or reduce enzymatic activities. Reduced temperatures may be conveniently obtained by using dry ice and/or liquid nitrogen.

According to the present invention, it is preferable to take and convert a portion of the tissue material having a weight of less than 1 g, in particular less than 0.5 g and especially less than 0.2 g or less than 0.1 g. On the other hand, the portion should allow the determination of the analyte. Therefore, said portion usually has a weight of at least 0.001 g, in particular at least 0.005 g, and especially at least 0.01 g. This portion is hereinafter also referred to as an aliquot.

For statistical reasons and improved reliability, it may be expedient to take samples from tissue material of separate biological organisms of the same species grown under similar conditions.

In one embodiment of the invention, the plant tissue material is comminuted to a fine powder. Generally, comminution comprises a step of milling the tissue material to yield the fine powder. This milling step can be carried out using any device known in the art to produce the desired particle size. According to a preferred embodiment, milling is ultracentrifugal milling, planetery ball milling and mixer milling. In addition to the milling step, the comminution step may further comprises sieving of the milled material so as to provide a powder having a more defined particle size. However, milling is not necessary in many cases. Milling and sieving can be conveniently combined in one and the same device. For instance, the mixer mill Retsch® MM 200, Retsch®MM 300, Retsch® MM 301 or Retsch® MM 400 has proven especially suitable for dry, wet and cryogenic milling. Other suitable mills include, for instance, the Retsch® ZM 100 ultracentrifugal mill, mortar grinder LC-102 (Gilson company), SPEX CertiPre 8000M Mixer/Mill (from SPEX CertiPre company), and planetary ball mills made by Retsch (supplied by GlenMills) and Fritsch (supplied by Gilson).

Prior to the milling step, it may be convenient to include a homogenization step, where the tissue material is homogenized, optionally comminuted and separated from impurities such as soil. Said homogenization can be carried out manually or using suitable devices such as mixers, cutters, grinders and/or sieves. For soil samples, homoloid mills such as FitzMILL®, e.g. model J and JT, have proven especially suitable. For plant material, cutting and mixing devices such as the Urschel Comitrol model 2600 food cutter, Stephan model 40 vertical cutter/mixer or Hobart HCM 450 vertical cutter/mixer have proven especially suitable.

As the sample is considered to usually represent a multi-component material, one objective of comminution is to homogenize the sample. A further objective of size reduction according to the present invention is the production of a desired particle size for extraction. In case the particle size is determined by sieve analysis (by shaking appropriate sieves for sufficient time to allow separation of those particle which pass the sieve and those which are retained, e.g. 30 minutes at 300 rpm), a powder having a particle size of 800 μm or less, in particular 700 μm or less, and especially 600 μm or less, 550 μm or less, 500 μm or less, 450 μm or less, or 400 μm or less, is considered to be a fine powder and expedient for the purposes of the invention. The particle size given here is the maximum diameter of the particles, which at least 90% by weight of the particles do not exceed ($D_{90}$ value), which can be easily determined by sieving.

The comminuted tissue material is subjected to an extraction in order to dissolve the analytes, i.e. the phytohormones, and to separate a first portion of the tissue matrix material. Preferably, only a portion of the powder is subjected to said extraction. Accordingly, the powder is preferably divided into at least two portions. The resulting portions can be essentially of the same size (volume or weight) or not.

As an alternative, in particular, if the tissue material has a small particle size, comminution and extraction can be performed as a single step, e.g. by comminution the plant material in at least a portion of the extractant. During the comminution of the tissue material in the liquid extractant, the particle size of the tissue material is reduced. With regard to the particle size, the above given values for powders also apply here. Prior to comminution, a homogenization may be performed as described above, if necessary.

Comminution in the extractant can be performed by any method and devices suitable for comminution of solid or semi solid material in a liquid, e.g. by wet milling. Suitable devices include but are not limited to ball mills, in particular planetary ball mills, e.g. Retsch® PM100, Retsch® PM100 CM, Retsch® PM200 or Retsch® PM 400, cryo mills, e.g. Retsch® CryoMill, mixer mills, e.g. Retsch® MM400 or Retsch® MM 200.

Extraction used in step i. is achieved by treatment of the powder with a liquid extractant. The extractant is a mixture of at least one water miscible neutral organic solvent having from 1 to 3 carbon atoms and 1 heteroatom selected from O and N with water containing from 0.1 to 5% by weight, in particular from 0.2 to 3% by weight, especially from 0.5 to 2% by weight, based on the extractant, of at least one acid. Thereby the analytes are extracted from the plant tissue material and a liquid extract containing the analyte is obtained.

The term "neutral organic solvent" has to be understood as a solvent which has no functional groups that are susceptible to significant protonation or deprotonation in water at pH between 4 to 8 and a temperature of 298 K. Significant protonation or deprotonation means an at least 10% protonation/deprotonation. Water miscibility means that the solvent is completely miscible with water at a temperature of 298 K. Suitable water miscible neutral organic solvent having from 1 to 3 carbon atoms and 1 heteroatom selected from O and N include but are not limited to $C_1$-$C_3$-alkanols such as methanol, ethanol, n-propanol, isopropanol and mixtures thereof, nitriles such as acetonitril and propionitril, and acetone.

Preferably, the organic solvent used in the extractant of step i. is selected from the group of $C_1$-$C_3$-alkanols. In particular, the organic solvent comprises at least 50 vol. %, in particular at least 70 vol. %, especially at least 90 vol. % of methanol, based on the total amount of organic solvent. Most preferably, the organic solvent is methanol.

The acid contained in the extractant used in step i. may be an inorganic acid, e.g. a hydrohalic acid such as hydrochloric acid, hydrobromic acid, or hydroiodic acid, perchloric acid, $HBF_4$, nitric acid or sulphuric acid, or an organic acid, e.g. a $C_1$-$C_3$-alkanoic acids, such as formic acid, acetic acid or propionic acid, a halogenated $C_1$-$C_3$-alkanoic acids such as chloroacetic acid, dichloroacetic acid, trichloroacetic acid or trifluoroacetic acid or an arylsulfonic acid such as benzenesulfonic acid or toluenesulfonic acid, and mixtures thereof. Preferably, the acid contained in the extractant is an organic acid, in particular a $C_1$-$C_3$-alkanoic acid such as formic acid, acetic acid or propionic acid or a mixture thereof. Especially, the acid is formic acid.

Preferably, the $C_1$-$C_3$-alkanol is methanol. The weight ratio of the organic solvent, in particular the $C_1$-$C_3$-alkanol, to water is preferably at least 1.5:1, in particular at least 2:1, e.g. in the range from 1.5:1 to 10:1, especially in the range from 2:1 to 5:1.

A particular preferred extractant used in step i. is a mixture of methanol with water containing from 0.1 to 5% by weight, in particular from 0.2 to 3% by weight, especially from 0.5 to 2% by weight, based on the extractant, of formic acid. In the particular preferred extractant the weight ratio of methanol to water is preferably at least 1.5:1, in particular at least 2:1, e.g. in the range from 1.5:1 to 10:1, especially in the range from 2:1 to 5:1.

The amount of extractant used in step i. will normally depend on the amount of comminuted plant tissue material to be extracted. A skilled person will readily find out the necessary amounts by routine experiments. Generally, the amount of extractant used in step i. will be about 10 to 200 mL, in particular from 15 to 100 mL per gram of tissue material to be extracted.

For calibration purposes, it might be useful to include a particular amount of at least one standard, preferably at least two or at least 3, in particular from 2 to 20 or from 3 to 10 standards, e.g. 2, 3, 4, 5 or 6 standards, into the extractant. These standards are normally themselves phytohormones or compounds which are chemically or structurally related to phytohormones. The compounds may be isotope labelled. In particular, endogenous standards will normally be labelled, while non-endogenous standards need not to be labeled. Preferred isotopes for labelling are non-radioactive isotopes. Preferred isotopes include but are not limited to deuterium ($^2$H), $^{15}$N and $^{13}$C, but they may also be labelled with $^{18}$O or $^{37}$Cl. The total concentration of standards in the extractant will depend from the type of analysis unit used. A skilled person can evaluate a suitable concentration by routine experiments. The total concentration of standards in the extractant will normally be from 0.05 to 100 ng/mL of extractant, in particular from 0.07 to 20 ng/mL or from 0.1 to 10 ng/mL. Examples of standards include e.g. $^{13}C_5$-adenine, $^2H_7$—$N^6$-benzyladenine, $^2H_7$—$N^6$-benzyladenosine, $^2H_7$—$N^6$-benzyladenine-3-glucoside, $^2H_7$—$N^6$-benzyladenine-7-glucoside, $^2H_7$—$N^6$-benzyladenine-9-glucoside, $^2H_7$—$N^6$-benzyladenosine-5'-mono-phosphate sodium salt, $^2H_3$-dihydrozeatin, $^2H_3$-dihydrozeatin riboside, $^2H_3$-dihydro-zeatin riboside-5'-monophosphate sodium salt, $^2H_3$-dihydrozeatin-9-glucoside, $^2H_7$-dihydrozeatin-O-glucoside, $^2H_7$-dihydrozeatin-O-glucoside riboside, $^2H_6$—$N^6$-isopentenyladenine, $2H_6$—$N^6$-isopentenyladenosine, $^{15}N_4$-isopentenyladenosine, $^2H_6$—$N^6$-isopentenyladenosine-5'-mono-phosphate sodium salt, $^2H_6$—$N^6$-isopentenyladenine-7-glucoside, $^2H_6$—$N^6$-isopentenyladenine-9-glucoside, $^2H_6$-2-methylthio-$N^6$-isopentenyl-adenosine, $^2H_6$-2-Methylthio-$N^6$-isopentenyladenine, $^{15}N_4$-kinetin, $^{15}N_4$-meta-topolin, $^{15}N_4$-ortho-topolin, $^2H_5$-trans-zeatin, $^{15}N$-trans-zeatin, $^2H_5$-trans-zeatin riboside, $^2H_5$-trans-zeatin-7-glucoside, $^2H_5$-trans-zeatin-9-glucoside, $^2H_5$-trans-zeatin-O-glucoside, $^2H_5$-trans-zeatin-O-glucoside riboside, $^2H_5$-trans-zeatin riboside-5'-monophosphate sodium salt, $^2H_5$-2-Methylthio-trans-zeatin, $^2H_5$-2-Methylthio-trans-zeatin riboside, $^2H_5$-indole-3-acetic acid, $^2H_5$-indole-3-acetic acid methyl ester, $^2H_2$-gibberellin A1, $^2H_2$-gibberelic acid, $^2H_2$-gibberellin A4, $^2H_2$-gibberellin A5, $^2H_2$-gibberellin A6, $^2H_2$-gibberellin A7, $^2H_2$-gibberellin A8, $^2H_2$-gibberellin A9, $^2H_2$-gibberellin A12, $^2H_2$-gibberellin A12 aldehyde, $^2H_2$-gibberellin A14, $^2H_2$-gibberellin A15, $^2H_2$-gibberellin A19, $^2H_2$-gibberellin A20, $^2H_2$-gibberellin A23, $^2H_2$-gibberellin A24, $^2H_2$-gibberellin A34, $^2H_2$-gibberellin A36, $^2H_2$-gibberellin A37, $^2H_2$-gibberellin A38, $^2H_2$-gibberellin A44, $^2H_2$-gibberellin A51, $^2H_2$-gibberellin A53, $^2H_2$-gibberellin A81, $^2H_2$-gibberellin A95, $^2H_2$-kaurene, $^2H_2$-kaurenol, $^2H_2$-kaurenal, $^2H_6$ (+)-cis, trans-abscisic acid and 2-chloro-6-aminopurin.

The treatment of the powder portion or aliquot with the liquid extractant in order to extract the analyte usually comprises agitating the powder extractant mixture. Agitating can involve, for instance, shaking, milling or sonicating or vortexing the sample. Usually, the treatment is carried out at temperatures in the range of −80 to <20° C. Lower or higher temperatures ranging from the melting to the boiling point of the solvent mixture used may, however, be expedient. Nonetheless, temperatures of 20° C. or higher are usually not required according to the present invention and thus can usually be avoided. Preferably the treatment is carried out at temperatures in the range of −80 to <10° C. Further, it is preferred that the treatment is carried out under atmospheric or near atmospheric pressure (about $10^5$ Pa, or in the range of 12 to 20 psi).

Also, it is preferred to separate the liquid extract from the remaining powder constituents, i.e. the matrix material, e.g. filtration or preferably by centrifugation, so that the liquid extract or a portion thereof is readily accessible and can be subjected to the subsequent steps.

In step ii. at least a portion of the liquid extract is contacted with a solid absorbent having a hydrophobically modified surface. Thereby, at least some of the hydrophobic material of the plant tissue which is not a phytohormone but which has been extracted in step i. and thus is contained in the extract as an impurity will become absorbed to the absorbent. Consequently, upon removing the solid absorbent from the extract after contact time will remove at least a portion of these hydrophobic impurities.

The phrase "removing the solid absorbent" is to be understood as a separation of the solid absorbent from the liquid extract after having contacted the liquid extract with the solid absorbent. Separation may include any measure of separating a solid from a liquid.

Contacting of the extract of step ii. with the hydrophobic absorbent and removal of the hydrophobic absorbent can be carried out e.g. as described for extraction of the plant tissue material. However, the contacting will be generally carried out at temperatures in the range from 5 to 40° C., e.g. at about ambient temperature, e.g. 20±5° C.

Step ii. can e.g. be performed by suspending the particulate absorbent in the liquid extract, followed by removal of the absorbent particles by filtration or sedimentation, e.g. by centrifugation. Step iv. can also be performed by conducting the liquid extract through a bed of the solid particulate absorbent, e.g. by filtration through a bed of the solid absorbent.

Suitable absorbent materials include hydrophobically modified silica, in particular alkyl modified silica, especially $C_8$-$C_{20}$-alkyl modified silica particles, and crosslinked polymer particles, in particular polymer particles comprising homo- or copolymers of divinylbenzene with neutral monoethylenically unsaturated monomers.

In a preferred embodiment of the invention, the absorbent is a particulate hydrophobically modified silica, in particular alkyl modified silica, especially $C_8$-$C_{20}$-alkyl modified silica such as $C_8$-alkyl or $C_{18}$-alkyl modified silica. Such hydrophobically modified silica is commercially available, e.g. for reversed phase liquid chromatography, and can be obtained as products sold under the following trade marks: Chromabond® C18 ec (Roth), Strata® C8-E (Phenomenex), Sep-Pak® tC18, Bond Elut® C18, DSC-18(Lt), ENVI®-18, LC-18, CLEAN-UP® C18, Bakerbond® Octadecyl, Isolute® C18(EC), LiChrolut® RP-18-E, Hysphere® C-18 HD (Spark Holland), Supelcosil®, e.g. Supelcosil® LC-8, Supelcosil® LC-18, ENVI®-8, ENVI®-18 (Sigma Aldrich), Fused-Core™ or Halo® (Advanced Materials Technology, Inc).

In another preferred embodiment of the invention, the absorbent is a polymeric absorbent based on crosslinked polymer particles, in particular an absorbent in the form of polymer particles comprising homo- or copolymers of divinylbenzene with neutral monoethylenically unsaturated monomers. Neutral monoethylenically unsaturated monomer is to be understood as a monomer having one C=C-double bond and containing no functional group which is capable of being significantly protonated or deprotonated in water at 25° C. and pH 1 to 12. The homo- or copolymers of divinylbenzene may form the polymer particles or may form a shell on a particulate polymeric carrier such as polystyrene. Suitable neutral comonomers include N-vinyl lactames, such as N-vinylpyrrolidone, vinylaromatics such as styrene, vinyltoluene or α-methylstyrene, nitriles such as acrylnitril or methacrylnitril, acrylamid, methacrylamid, N-vinylamides of saturated aliphatic acids, such as N-vinylacetamid, acrylate esters and methacrylate esters such as $C_1$-$C_{18}$-alkylacrylates, $C_1$-$C_{18}$-alkylmethacrylates, $C_5$-$C_8$-cycloalkylacrylates, $C_5$-$C_8$-cycloalkylmethacrylates, phenoxy-$C_2$-$C_4$-alkylmethacrylates, phenoxy-$C_2$-$C_4$-alkylmethacrylates, hydroxy-$C_2$-$C_4$-alkylacrylates and hydroxy-$C_2$-$C_4$-alkylmethacrylates.

Suitable organic polymeric absorbents based on crosslinked polymer particles are commercially available, e.g. for reversed phase liquid chromatography, and can be obtained as products sold under the following trade marks: Chromabond® HR—X (Roth), Chromabond® Easy (Roth), ENVI-Chrom P (Sigma-Aldrich), Strata®-X (Phenomenex), OASIS® HLB (Waters), Porapak® RDX (Waters), Nexus® (Varian), Bond Elut® PPL (Varian), Focus® (Varian), Styre Screen® DVB (United Chemical Technologies—UCT), Bakerbond® $H_2O$ philic DVB (Avantor® Performance Materials—purchases JT Backer brands), Isolute® ENV+0 (Biotage).

The particle size of solid absorbent used in step ii. will generally be in the range from 1 to 100 μm, in particular from 3 to 50 μm (weight average as determined by sieving).

For performing step ii. it is required to contact the extract with a sufficient amount of a hydrophobic absorbent. The amount of solid absorbent used in step ii. will generally be in the range from 1 mg to 3000 mg per ml of extract which is contacted with the absorbent.

Step ii. can e.g. be performed by suspending the particulate absorbent in the liquid extract, followed by removal of the absorbent particles by filtration or sedimentation, e.g. by centrifugation. Step ii. can also be performed by conducting the liquid extract through a bed of the solid particulate absorbent, e.g. by filtration through a bed of the solid absorbent.

In a preferred embodiment of the invention, step ii. is carried out as a filtration of the first liquid extract over a column containing the solid absorbent. In a particular preferred embodiment step ii. is carried out as a solid phase extraction (SPE) by using a solid phase extraction cartridge containing the solid absorbent. The cartridges may have the form of a single tube containing the absorbent or may be a plate containing a multitude of tubes for parallel use. In the cartridge, the amount of absorbent will generally be in the range from 5 to 1000 mg, per tube. Suitable cartridges for solid phase extraction containing the solid absorbent are commercially available, e.g. as OASIS® HLB columns and cartridges from Waters, the Supelco® SPE columns and cartridges from Supelco (Sigma-Aldrich), the Chromabond® columns and cartridges from Macherey-Nagel, Isolute® columns and cartridges (Biotage), GracePure SPE cartridges or columns (GRACE), 3M™ Empore cartridges or columns (Sigma-Aldrich), Evolute (Biotage), PoraPak Rxn RP or Sep-Pak cartridges and columnsn (Waters), Strata SPE columns and cartridges (Phenomenex), Chromafix RP columns and cartridges (Machery-Nagel), or LiChrolut® (Merck).

Filtration and SPE will be generally carried out at temperatures in the range from 5 to 40° C., e.g. at about ambient temperature, e.g. 20±5° C.

Filtration or SPE, respectively, is generally followed by a washing step. In the washing step, the absorbent in the column, in particular the absorbent in the SPE cartridge is washed with a sufficient amount of extractant in order to avoid loss of analyte. The amount of extractant used for washing will generally be in the range from 10 to 100% by volume of the extract.

It has been found to be advantageous to pre-treat the absorbent material with at least a part of the solvents contained in the extractant, in particular if step ii. is carried out as a filtration or especially as an SPE, in order to achieve a pre-conditioning an optionally an equilibration of the absorbent material. Pre-treatment will generally include a pre-conditioning step of contacting the absorbent with at least one water miscible neutral organic solvent having from 1 to 3 carbon atoms and 1 heteroatom selected from O and N as defined above, in particular with an organic solvent selected from $C_1$-$C_3$-alkanols, especially methanol, which is optionally followed by an equilibration step, where the preconditioned absorbent material is contacted with a mixture of said organic solvent and water containing from 0.1 to 5% by weight, especially from 0.5 to 2% by weight, based on water, of at least one acid as defined above, in particular at least one organic acid as defined above, especially at least one $C_1$-$C_3$-alkanoic acid as defined above. e.g. formic acid, or with a mixture of water containing from 0.1 to 5% by weight, especially from 0.5 to 2% by weight, based on water, of at least one acid as defined above, in particular at least one organic acid as defined above, especially at least one $C_1$-$C_3$-alkanoic acid as defined above, e.g. formic acid. Preferably, the pre-treatment includes (1) a preconditioning step which is preferably achieved by treating the absorbent material with at least one $C_1$-$C_3$-alkanol, especially methanol, or with a mixture thereof with water; and an equilibration step which is performed by treating the preconditioned absorbent material with water containing from 0.1 to 5% by weight, especially from 0.5 to 2% by weight, based on water, of at least one acid as defined above, in particular at least one organic acid as defined above, especially at least one $C_1$-$C_3$-alkanoic acid as defined above, e.g. formic acid, or with a mixture of water with a $C_1$-$C_3$-alkanol, especially methanol, containing from 0.1 to 5% by weight, especially from 0.5 to 2% by weight, based on water, of at least one acid as defined above, in particular at least one organic acid as defined above, especially at least one $C_1$-$C_3$-alkanoic acid as defined above, e.g. formic acid.

In step iii. of the process of the present invention, the solvent from the second extract is evaporated. Thereby, a residue is obtained, which is re-dissolved in a solvent mixture to obtain a reconstituted extract. For re-dissolving, a solvent mixture of at least one $C_1$-$C_3$-alkanol with water is used, which solvent mixture contains from 0.1 to 5% by weight, based on the solvent mixture, of at least one acid, preferably at least one acid as defined above, in particular at least one organic acid as defined above, especially at least one $C_1$-$C_3$-alkanoic acid as defined above, e.g. formic acid.

Evaporation is normally achieved by applying vacuum, e.g. from atmospheric pressure (1013 mbar) to 10 mbar to the second extract obtained in step ii. Evaporation is normally carried out at temperatures ranging form 0 to 50° C., in particular from 10 to 40° C. Generally, the solvent is removed until a dry or virtually dry residue is obtained. The residue will generally contain less than 20% of solvent, based on the weight of the residue.

Dissolution of the residue in step iii. is achieved by treatment of the residue with a solvent mixture, which is a mixture of at least one water miscible neutral organic solvent having from 1 to 3 carbon atoms and 1 heteroatom selected from O and N as defined above, with water containing from 0.1 to 5% by weight, in particular from 0.2 to 3% by weight, especially from 0.5 to 2% by weight, based on the mixture, of at least one acid. Thereby the analytes and optionally the standards contained in the extract of step ii. are re-dissolved and a reconstituted liquid extract is obtained, which contains the analyte and the optional standard, if added in step i.

Preferably, the organic solvent used in the solvent/water mixtures of step iii. is selected from the group of $C_1$-$C_3$-alkanols. In particular, the organic solvent comprises at least 50 vol. %, in particular at least 70 vol. %, especially at least 90 vol. % of methanol, based on the total amount of organic solvent. Most preferably, the organic solvent is methanol. In this mixture, the weight ratio of the organic solvent, in particular the $C_1$-$C_3$-alkanol, to water is generally at most 1:1, preferably at most 1:1.5, in particular at most 1:2, e.g. in the range from 1:1 to 1:15, frequently in the range from 1:1.5 to 1:10, especially in the range from 1:2 to 1:5.

The acid contained in the solvent mixture used in step iii. may be an inorganic acid, e.g. a hydrohalic acid such as hydrochloric acid, hydrobromic acid, or hydroiodic acid, perchloric acid, $HBF_4$, nitric acid or sulphuric acid, or an organic acid, e.g. a $C_1$-$C_3$-alkanoic acids, such as formic acid, acetic acid or propionic acid, a halogenated $C_1$-$C_3$-alkanoic acids such as chloroacetic acid, dichloroacetic acid, trichloroacetic acid or trifluoroacetic acid or an arylsulfonic acid such as benzenesulfonic acid or toluenesulfonic acid, and mixtures thereof. Preferably, the acid contained in the extractant is an organic acid, in particular a $C_1$-$C_3$-alkanoic acid such as formic acid, acetic acid or propionic acid or a mixture thereof. Suitable $C_1$-$C_3$-alkanols include methanol, ethanol, n-propanol and isopropanol and mixtures thereof.

A particular preferred solvent mixture used in step iii. is a mixture of methanol with water containing from 0.1 to 5% by weight, in particular from 0.2 to 3% by weight, especially from 0.5 to 2% by weight, based on the extractant, of formic acid. In the particular preferred extractant the weight ratio of methanol to water is preferably at most 1:1, in particular at most 1:2, e.g. in the range from 1:1 to 1:10, especially in the range from 1:2 to 1:5.

The amount of solvent mixture used in step iii. will normally depend on the amount of residue to be reconstituted. A skilled person will readily find out the necessary amounts by routine experiments. Generally the amount of solvent mixture will be from 5 µL to 5000 µL, in particular from 10 to 500 µL, per mg of starting material, i.e. the residue to be reconstituted.

The treatment of the residue with the solvent mixture is achieved by adding at least a portion of the solvent mixture or the complete solvent mixture to the residue. If the solvent mixture is added in more than one portion, e.g. in 2, 3, or 4 portions, preferably, the portion which is added first has a higher concentration of organic solvent, in particular $C_1$-$C_3$-alkanol, than the overall concentration of organic solvent, in particular $C_1$-$C_3$-alkanol, in the mixture.

The treatment of the residue with the solvent mixture to dissolve the analyte usually comprises agitating the residue extractant mixture. Agitating can involve, for instance, shaking, sonicating or vortexing the sample. Usually, the treatment is carried out at temperatures in the range of −10 to <30° C. Lower or higher temperatures ranging from the melting to the boiling point of the solvent mixture used may, however, be expedient. Nonetheless, temperatures of 30° C. or higher are usually not required according to the present invention and thus can usually be avoided. Preferably the treatment is carried out at temperatures in the range of 0 to 25° C. Further, it is preferred that the treatment is carried out under atmospheric or near atmospheric pressure (about $10^5$ Pa, or in the range of 12 to 20 psi).

At least a portion or all of the reconstituted extract is then subjected to a further purification in step iv. followed by step v. of the method of the present invention.

In step iv. of the method according to the present invention, the reconstituted extract of step iii. is subjected to a further purification step, which includes contacting the reconstituted extract of step iii. with a solid absorbent having a hydrophobically modified surface. Thereby a purified reconstituted extract is obtained, which hereinafter is also termed as eluate or eluate of step iv, respectively.

Principally, step iv. can be carried out e.g. as described for step ii.

Suitable absorbent materials for step iv. include hydrophobically modified silica, in particular alkyl modified silica, especially $C_6$-$C_{20}$-alkyl modified silica particles, and crosslinked polymer particles, in particular polymer particles comprising homo- or copolymers of divinylbenzene with neutral monoethylenically unsaturated monomers.

In a preferred embodiment of the invention, the absorbent of step iv. is a particulate hydrophobically modified silica, in particular alkyl modified silica, especially $C_6$-$C_{20}$-alkyl modified silica such as $C_8$-alkyl or $C_{18}$-alkyl modified silica as described for step ii.

In another preferred embodiment of the invention, the absorbent of step iv. is a polymeric absorbent based on crosslinked polymer particles, in particular an absorbent in the form of polymer particles comprising homo- or copolymers of divinylbenzene with neutral monoethylenically unsaturated monomers as described for the polymeric absorbents of step ii. Suitable organic polymeric absorbents based on crosslinked polymer particles are commercially available, e.g. for reversed phase liquid chromatography, and can be obtained as products as described for step ii.

The particle size of solid absorbent used in step iv. will generally be in the range from 1 to 100 μm, in particular from 3 to 50 μm (weight average as determined by sieving).

For performing step iv. it is required to contact the extract with a sufficient amount of a hydrophobic absorbent. The amount of solid absorbent used in step iv. will generally be in the range from 10 to 850 μl per ml of extract which is contacted with the absorbent.

Step iv. can e.g. be performed by suspending the particulate absorbent in the liquid extract, followed by removal of the absorbent particles by filtration or sedimentation, e.g. by centrifugation. Step iv. can also be performed by conducting the liquid extract through a bed of the solid particulate absorbent, e.g. by filtration through a bed of the solid absorbent.

In a preferred embodiment of the invention, step iv. is carried out as a filtration of the reconstituted extract over a column containing the solid absorbent. In a particular preferred embodiment step iv. is carried out as a solid phase extraction (SPE) as described for step ii. by using a solid phase extraction cartridge containing the solid absorbent.

In step iv. of the present invention, contacting, in particular filtration and SPE, respectively, will be generally carried out at temperatures in the range from 4 to 40° C., e.g. at about ambient temperature.

Filtration or SPE, respectively, is generally followed by a washing step. In the washing step, the absorbent in the column, in particular the absorbent in the SPE cartridge is washed with a sufficient amount of solvent in order to avoid loss of analyte. The amount of solvent used for washing will generally be in the range from 10 to 300% by volume of the reconstituted extract. The type of solvent for washing is generally the solvent used in step v. of the present invention, e.g. the solvent used for the liquid chromatography in step v. of the process of the present invention.

It has been found to be advantageous to pre-treat the absorbent material of step iv. with at least one organic solvent, in particular if step iv. is carried out as a filtration or especially as an SPE, in order to achieve a preconditioning and optionally an equilibration of the absorbent material. Pre-treatment is preferably carried out by contacting the absorbent with the solvent or solvent mixture used in step v., e.g. the solvent or solvent mixture used for the reversed phase LC-MS in step v. of the inventive process. Pre-treatment may also be carried out by using only water. Preferably, the pre-treatment includes a preconditioning step which is achieved by treating the absorbent material with an organic solvent, which is completely miscible with water, or a mixture thereof with water. Suitable solvents, which are miscible with water include the aforementioned neutral organic solvents, in particular $C_1$-$C_3$-alkanols, but also tetrahydrofurane, dioxane, $C_3$-$C_4$-ketones such as acetone and acetonitril and mixtures thereof, with acetonitril and acetone being particularly preferred. Preferably, the preconditioning step is followed by an equilibration which is generally achieved by treating the preconditioned absorbent material with water or a mixture of water with an organic solvent, which is completely miscible with water, wherein the pH of water or the mixture of water has been preferably adjusted by acid or base or by a buffer. The pH is preferably adjusted to be in the range of from 4 to 8, in particular from 4.5 to 7 and especially from 5 to 6, at 20° C. In particular, the water or water mixture used for equilibration contains a buffer. Suitable buffers include ammonium salts of $C_1$-$C_3$-alkanoic acids, e.g. ammoniumformiate or ammonium acetate, and ammonium salts of other weak acids such as ammonium hydrogencarbonate, ammoniumbicarbonate and ammoniumfluorid and mixtures thereof. The concentration of the buffer in the solvent will preferably be in the range from $10^{-3}$ to $10^{-1}$ mol $L^{-1}$, in particular from $5\times10^{-3}$ to $5\times10^{-2}$ mol $L^{-1}$.

As pointed out above, step iv. is preferably carried out as a solid phase extraction. In a particular embodiment, the solid phase extraction cartridge containing the solid absorbent is directly, i.e. online, coupled to the analyzing unit, such as column for liquid chromatography (LC). Hence, the eluate of the SPE cartridge is directly transferred to the separation unit of the analyzing unit. Suitable cartridges, which can be coupled directly to the separation unit of the analyzing unit, such as a LC-column are commercially available.

In step v. the reconstituted and purified extract is transferred to an analyzing unit which comprises a separation unit and an analyzer for identifying the phytohormones. The separation unit serves for an at least partial separation or resolution of the phytohormones contained in the reconstituted and purified extract of step iv. Separation or resolution can be achieved by any measures suitable for separating resolving the individual phytohormones contained in a mixtures of phytohormones. Normally the separation unit is a chromatographic unit, e.g. a unit for liquid chromatography LC.

Preferably, the separation unit is a unit for performing liquid chromatography, in particular reverse phase LC.

Reverse phase LC in step v. can be carried out by analogy to reverse phase LC of phytohormone mixtures, as described in the art. Suitable LC techniques include in particular high performance LC (also termed HPLC) and ultrahigh performance LC (also termed UPLC). For the purposes of the present invention HPLC will provide sufficient resolution of the analytes.

In the reverse phase LC in step v. the analytes contained in the reconstituted extract of step iv. are separated, i.e. resolved with regard to their retention time, i.e. with regard to their partition between the mobile phase (eluent) and the stationary phase. The resolved analytes are then identified in the analyzer.

In the reverse phase LC, the stationary phase is generally a hydrophobic absorbent. Suitable absorbent materials for reverse phase LC of step v. include hydrophobically modified silica, in particular alkyl modified silica, especially $C_6$-$C_{20}$-alkyl modified silica such as $C_8$-alkyl or $C_{18}$-alkyl modified silica and absorbents based on organic polymers as described in step ii.

In the reverse phase LC, the mobile phase (eluent) is generally an organic solvent or solvent mixture, which organic solvent is completely miscible with water or a mixture of water with at least one organic solvent, which is completely miscible with water. Examples of suitable organic solvents which are completely miscible with water include the aforementioned $C_1$-$C_3$-alkanols, tetrahydrofurane, dioxane, $C_3$-$C_4$-ketones such as acetone and acetonitril and mixtures thereof, with acetonitril and acetone being particularly preferred.

The eluent may contain an acid or a base or a buffer for adjusting the pH of the eluent. The pH of the eluent will be generally in the range from 4 to 8, in particular from 4.5 to 7 and especially from 5 to 6, at 20° C. Preferably, the eluent used in the reverse phase LC of step v. contains at least one buffer. Suitable buffers include ammonium salts of $C_1$-$C_3$-alkanoic acids, e.g. ammoniumformiate or ammonium acetate, and ammonium salts of other weak acids such as ammonium hydrogencarbonate, ammonium carbonate, ammoniumbicarbonate and ammoniumfluorid. The concentration of the buffer in the eluent will preferably be in the range from $10^{-3}$ to $10^{-1}$ mol $L^{-1}$, in particular from $5 \times 10^{-3}$ to $5 \times 10^{-2}$ mol $L^{-1}$.

In a particular preferred embodiment of the invention, the reverse phase LC of step v. is carried out by using a gradient of mixture of water with at least one organic solvent, which is completely miscible with water, which mixture contains a buffer. Suitable buffers are those mentioned above. Generally, the ratio of organic solvent to water in the gradient will increase during a run.

In step v., reverse phase LC will be generally carried out at temperatures in the range of ambient temperature, e.g. from 10 to 40° C.

As pointed out above, the separation unit in step v. leads to a resolution of the analytes, e.g. with regard to their retention time if a chromatographic method is used. By coupling separation unit, e.g. a LC-column, with the analyzer, the resolved analytes can then detected and identified, e.g. by characteristics such as their molecular or quasimolecular ion and or by their MS/MS fragmentation pattern, if mass spectrometry is used for identification of the phytohormones.

Preferred techniques for analyzing/identifying the phytohormones are mass spectrometry based techniques (MS), including Fourier transform ion-cyclotrone-resonance mass spectrometry (FT-ICR-MS), time of flight mass spectrometry (TOF or TOF-MS), ion mobility mass spectrometry (IMS), direct infusion mass spectrometry, quadrupole mass spectrometry, sector-field mass spectrometry, Orbitrap mass spectrometry or any sequentially coupled mass spectrometry, such as MS-MS or MS-MS-MS. Ionization can be performed e.g. by electron impact ionization (EI), electro spray ionization (ESI) or atmospheric pressure chemical ionization (APCI).

Preferably, step v. is performed by using one of the following techniques:

Liquid chromatography coupled MS, in particular high-performance liquid chromatography coupled mass spectrometry (HPLC-MS) or ultra high performance liquid chromatography (UPLC, uHPLC) coupled with mass spectrometry (MS), in particular coupled with ion mobility mass spectrometry or direct infusion mass spectrometry, especially coupled with electro spray ionization MS (ESI-MS) or atmospheric pressure chemical ionization MS (APCI-MS).

Said techniques are described in, e.g., Niessen, Journal of Chromatography A, 703, 1995: 37-57, U.S. Pat. No. 4,540,884 or U.S. Pat. No. 5,397,894, the disclosure content of which is hereby incorporated by reference.

Most preferably, HPLC, especially reverse phase HPLC coupled with MS, in particular coupled with ESI-MS and especially with ESI-MS/MS is used in step v. as the analyzing unit. APCI can be used instead of ESI.

In a particular embodiment of the invention, ESI-MS or APCI-MS is used for detecting/identifying the resolved phytohormones. In a very particular embodiment of ESI-MS there is a switch between negative electrospray ionisation and positive electrospray ionisation, which is optionally combined with a Q3 scan in the positive mode or in the negative mode in order to reduce selectivity in order to detect a larger number of analytes in the range from 150 to 600 Da. Detection is preferably achieved by multiple reaction monitoring (MRM) in combination with a full scan.

Reproducibility of the method can be controlled by internal standards as described before or by repeatedly including into the sequence of measurements an analysis of stock solutions of standards containing known concentrations of analytes. Calibration of retention time and peak form can be controlled by measuring a sample of a standard compound in solvent or including a standard compound into the extract.

The method of the present invention allows in a reliable and easy way to simultaneously determine phytohormone levels of multitude of phytohormones in plant tissue material or tissue material of other plastid containing organisms, i.e. the level of at least 2, frequently at least 4, in particular at least 6, especially at least 8 or at least 10 phytohormone, e.g. from 2 to 60, frequently from 4 to 50, in particular from 6 to 45, especially from 8 to 40 or from 10 to 30 phytohormones in one sample of the plant material at the same time. Examples of phytohormones, which can be simultaneously determined, include but are not limited to, the following: Dihydrozeatin-7-glucosides, meta-topolin, ortho-topolin, trans-zeatin-9-glucoside, trans-zeatin, trans-zeatin riboside, trans-zeatin riboside-O-glucoside, trans-zeatin-O-glucoside, cis-zeatin riboside-O-glucoside, dihydrozeatin riboside-O-glucoside, dihydrozeatin-O-glucosides, isopentenyl adenine, isopentenyl adenosine, abscisic acid, abscisic acid glucosyl ester, indol-3-acetyl aspartic acid, indole-3-acetyl-alanine, indole-3-acetyl-tryptophan, cis-zeatin, indol-3-acetic acid, indol-3-carboxylic acid, indole-3-acetyl-glutamic acid, indol-3-acetic acid methyl ester, tryptamine, tryptophan, jasmonic acid and salicylic acid and the derivatives of salicylic acid, e.g. the esters of salicylic acid.

The method of the present invention is particular useful for determining simultaneously a multitude of phytohormones including the phytohormones jasmonic acid and salicylic acid and its derivates, e.g. the esters of salicylic acid.

The invention is hereinafter described in more detail by way of examples.

I Material

1. Equipment for Sample Preparation

For step ii. a 96 well SPE plate (OASIS HLB plate, Waters), including a vacuum system for off-line SPE was used.

2. Equipment for Separation and Detection

For steps iv. and v. a commercial equipment for combined SPE and HPLC (Symbiosis Pharma Online-SPE/HPLC-Spark Holland), including a SPE cartridge (Spark Holland) and a HPLC column (GRACE) which was coupled with a conventional triple quadrupol mass spectrometer API 5500 (Applied Biosystems).

3. Chemicals formic acid 98-100% (p.a.);
acetonitrile (LC-MS grade);
water ultrapure (Milli-Q water system);
methanol (HPLC grade)

As an internal standard a mixture of the following compounds was used:

| Internal standards: |
| --- |
| [$^2H_5$]indole-3-acetic acid |
| 2-chloro-6-aminopurin |
| [$^2H_3$]dihydrozeatin |
| [$^2H_5$]trans-zeatin |
| [$^{15}N_4$]ortho-topolin |
| [$^2H_6$](+)-cis,trans-abscisic acid |

The following solvents for online SPE/HPLC (steps iv. and v.) were used:
solvent 1 (SPE module): 15 mM solution of ammonium formiate in water,
solvent 2 (SPE module): acetonitrile,
solvent A (HPLC): 15 mM solution of ammonium formiate in water,
solvent B (HPLC): 15 mM solution of ammonium formiate in acetonitrile:water (9:1, v/v), For identification purposes a mixture of phytohormones is used (Table 1)

TABLE 1

| Phytohormone mixture for stock solution Phytohormone |
| --- |
| 12-oxo-phytodienoic acid |
| 4-chloroindole-3-acetic acid |
| Abscisic acid |
| Abscisic acid glucosyl ester |
| Benzyladenine |
| cis-zeatin riboside-O-glucoside |
| Dihydrozeatin |
| Dihydrozeatin riboside-O-glucoside |
| Dihydrozeatin-7-glucosides |
| Dihydrozeatin-9-glucosides |
| Dihydrozeatin-O-glucosides |
| Indole-3-acetic acid |
| Indole-3-acetyl aspartic acid |
| indole-3-acetic acid methyl ester |
| Indole-3-acetonitril |
| Indole-3-acetyl-alanine |
| indole-3-acetyl-glutamic acid |
| Indole-3-acetyl-isoleucine |
| Indole-3-acetyl-leucine |
| Indole-3-acetyl-phenylalanine |
| Indole-3-acetyl-tryptophan |
| Indole-3-acetyl-valine |
| indole-3-butyric acid |

TABLE 1-continued

| Phytohormone mixture for stock solution Phytohormone |
| --- |
| Indole-3-carboxylic acid |
| Isopentenyl adenine |
| isopentenyl adenosine |
| Jasmonic acid |
| jasmonic acid methyl ester |
| Kinetin |
| Kinetin riboside |
| meta-topolin |
| ortho-topolin |
| salicylic acid |
| trans-Zeatin riboside |
| trans-zeatin riboside-O-glucoside |
| trans-zeatin-9-glucoside |
| trans-zeatin-O-glucoside |
| tryptamine |
| tryptophan |
| Cis-Zeatin (cis) |
| Trans-Zeatin (trans) |

4. Analytical Procedure 4.1 Sample Preparation, General Description (Steps i. to iii.)

Freeze-dried and particulated plant material was weighted into 2 ml Eppendorf vials with an accuracy of +/−0.5 mg.

Net weights
Corn leaf: 30 mg
Corn cob: 30 mg
Lemna: 15 mg

To the plant material 1 ml of ice-cold (−80° C.) extraction solvent (methanol/water (4:1, v/v)+1 vol-% formic acid) that contains the internal standard (4 ng/ml) was added. After addition of steel balls the plant material was extracted using a ball mill for 30 sec at 30 Hz. Afterwards the sample was centrifuged at 4° C. for 15 min at 10,000 rpm. The supernatant was removed and applied to an off-line SPE plate (96-well, Oasis HLB, Waters) which had been conditioned with methanol and equilibrated with 1 vol-% aqueous formic acid. The eluate was collected in a glass vial (within a 96-well plate). The SPE material was then washed once with the extraction solvent. The eluate of the washing step was collected in the same vial as the eluate of the sample and the combined eluates were evaporated to dryness. The residue was resuspended in a mixture of methanol and water (1:4 (v/v)) containing 1.5 vol-% aqueous formic acid. The samples were transferred to a 96-well plates for analysis.

4.2 Online SPE-LC/MS/MS Method (Steps iv. and v.)

4.2.1 General Description

Before injecting the sample, the SPE cartridge was conditioned with solvent 2 and equilibrated with solvent 1. After the injection of 20 μl of the reconstituted eluate, the sample was transferred to the SPE cartridge. Components of the matrix were removed by washing with solvent 1.

Afterwards the cartridge was eluted over 11 minutes with an LC chromatography gradient by which the metabolites were eluted and separated. The chromatographic gradient between solvent A (95%) and Solvent B (5%), where the concentration of solvent A was decreasing and the concentration of solvent B was increasing over time, was processed at a constant flow of 0.35 ml/min and a column oven temperature of 35° C. was maintained.

Data regarding the target metabolites were acquired using the highly selective MRM (multiple reaction monitoring) detection with positive/negative switch in combination with a Q3 scan (150-600 Dalton) in positive mode. Data were processed using the Quantitation Tool in Analyst 1.5.1.

Using the analyte peak area observed in the chromatogram allows the relative quantification of two samples (control (not the standard) versus sample). If an internal standard is used in both a sample and a standard sample, an absolute quantification is possible using a single point calibration curve (through the origin).

The reproducibility of the measurement was monitored by internal standards as well as by repeatedly measuring control samples during the test sequence. The retention time and the peak form were controlled on the basis of a sample of all standard compounds in solvent alone and in matrix.

TABLE 1

Overview of analytes measured in Corn leaf samples
Corn Leaf

Abscisic acid
Abscisic acid glucosyl ester
cis-Zeatin riboside-O-glucoside
Dihydrozeatin riboside-O-glucoside
Dihydrozeatin-O-glucosides
Indol-3-acetic acid methyl ester
Indol-3-carboxylic acid
Isopentenyl adenine
Isopentenyl adenosine
Jasmonic acid
Salicylic acid
Tryptamine
Tryptophan

TABLE 2

Overview of analytes measured in Corn cob samples
Corn Cob

Abscisic acid
Abscisic acid glucosyl ester
cis Zeatin
cis-Zeatin riboside-O-glucoside
Dihydrozeatin riboside-O-glucoside
Dihydrozeatin-7-glucosides
Dihydrozeatin-O-glucosides
Indol-3-acetic acid
Indol-3-acetic acid methyl ester
Indol-3-acetyl aspartic acid
Indole-3-acetyl-alanine
Indole-3-acetyl-glutamic acid
Indole-3-acetyl-tryptophan
Isopentenyl adenine
Isopentenyl adenosine
Jasmonic acid
Salicylic acid
Corn Cob
trans-Zeatin
trans-Zeatin riboside
trans-Zeatin riboside-O-glucoside
trans-Zeatin-9-glucoside
trans-Zeatin-O-glucoside
Tryptamine
Tryptophan

TABLE 3

Overview of analytes measured in Lemna samples
Lemna

Abscisic acid
Abscisic acid glucosyl ester
cis Zeatin
cis-Zeatin riboside-O-glucoside
Dihydrozeatin riboside-O-glucoside
Dihydrozeatin-O-glucosides
Indol-3-acetic acid
Indol-3-acetic acid methyl ester
Indol-3-carboxylic acid
Indole-3-acetyl-glutamic acid
Isopentenyl adenine
Isopentenyl adenosine
Jasmonic acid
meta-Topolin
ortho-Topolin
Salicylic acid
trans-Zeatin
trans-Zeatin riboside
trans-Zeatin riboside-O-glucoside
trans-Zeatin-O-glucoside
Tryptamine
Tryptophan

We claim:

1. A method for profiling phytohormone levels in tissue of a plastid containing organism, the method comprising,
   i. extracting particulate tissue material of the plastid containing organism with a liquid extractant, which is a mixture of at least one water miscible neutral organic solvent having from 1 to 3 carbon atoms and 1 heteroatom selected from O and N with water containing from 0.1 to 5% by weight, based on the extractant, of at least one acid, whereby a first liquid extract is obtained;
   ii. contacting the liquid extract obtained in step i. with a solid absorbent having a hydrophobically modified surface and removing the solid absorbent to obtain a second liquid extract;
   iii. evaporating the solvent from the second extract to obtain a residue and then re-dissolving the obtained residue in a solvent mixture of at least one water miscible neutral organic solvent having from 1 to 3 carbon atoms and 1 heteroatom selected from O and N with water containing from 0.1 to 5% by weight, based on the solvent mixture, of at least one acid to obtain a reconstituted extract;
   iv. purifying the reconstituted extract by passing it through a bed of a solid absorbent having a hydrophobically modified surface to obtain a purified reconstituted extract; and
   v. determining relative concentrations of at least two plant hormones in the purified reconstituted extract obtained in step iv. by directly subjecting the purified reconstituted extract to an analyzing unit comprising a separation unit for separation of the phytohormones and an analyzer for identifying the phytohormones which separation unit is coupled to the analyzer;
   wherein step iv. is performed as a solid phase extraction by using a solid phase extraction cartridge containing the solid absorbent; wherein the solid phase extraction cartridge is directly coupled to a column of a reverse phase LC-MS; and wherein the solid absorbent of step iv. is selected from the group consisting of $C_6$-$C_{20}$-alkyl modified silica particles and polymer particles comprising homo or copolymers of divinylbenzene with neutral monoethylenically unsaturated monomers.

2. The method of claim 1, wherein step ii, is performed by passing the first liquid extract through a bed of the solid absorbent.

3. The method of claim 2, wherein step ii. is performed as a solid phase extraction by using a solid phase extraction cartridge containing the solid absorbent.

4. The method of claim 1, wherein the solid absorbent which is contacted with the first extract is selected from $C_6$-$C_{20}$-alkyl modified silica particles and polymer particles comprising homo or copolymers of divinylbenzene with neutral monoethylenically unsaturated monomers.

5. The method of claim 1, wherein the acid contained in the extractant is selected from $C_1$-$C_3$-alkanoic acids, hydrohalic acid, halogenated $C_1$-$C_3$-alkanoic acids, perchloric acid, $HBF_4$, sulphuric acid, nitric acid and arylsulfonic acids and mixtures thereof.

6. The method of claim 5, wherein the extractant is a mixture of a $C_1$-$C_3$-alkanol with water containing from 0.1 to 5% by weight, based on the extractant, of formic acid.

7. The method of claim 6, wherein the extractant is a mixture of methanol with water containing from 0.1 to 5% by weight, based on the extractant, of formic acid.

8. The method of claim 1, wherein the acid contained in the solvent mixture used in step iii. is selected from $C_1$-$C_3$-alkanoic acids, hydrohalic acids, halogenated $C_1$-$C_3$-alkanoic acids, perchloric acid, $HBF_4$, sulphuric acid, nitric acid and arylsulfonic acids and mixtures thereof.

9. The method of claim 8, wherein the solvent mixture used in step iii. is a mixture of a $C_1$-$C_3$-alkanol with water containing from 0.1 to 5% by weight, based on the solvent mixture, of formic acid.

10. The method of claim 9, wherein the solvent mixture used in step iii. is a mixture of methanol with water containing from 0.1 to 5% by weight, based on the solvent mixture, of formic acid.

11. The method of claim 1, wherein the separation unit is a unit for reversed phase liquid chromatography and where the analyzer is a unit for mass spectrometry.

12. The method of claim 11, wherein the reversed phase liquid chromatography is performed by using a gradient of mixture of water with at least one organic solvent, which is completely miscible with water, which mixture contains a buffer.

13. The method of claim 11, wherein the mass spectrometry is performed as electrospray ionization mass spectrometry.

14. The method of claim 1, wherein at least two labelled phytohormones are included into the liquid extractant as an internal standard.

15. The method of claim 1, wherein the phytohormones to be analyzed include at least four compounds from the following list:

Dihydrozeatin-7-glucosides, meta-topolin, ortho-topolin, trans-zeatin-9-glucoside, trans-zeatin, trans-zeatin riboside, trans-zeatin riboside-O-glucoside, trans-zeatin-O-glucoside, cis-zeatin riboside-O-glucoside, dihydrozeatin riboside-O-glucoside, dihydrozeatin-O-glucosides, isopentenyl adenine, isopentenyl adenosine, abscisic acid, abscisic acid glucosyl ester, indol-3-acetyl aspartic acid, indole-3-acetyl-alanine, indole-3-acetyl-tryptophan, cis-zeatin, indol-3-acetic acid, indol-3-carboxylic acid, indole-3-acetyl-glutamic acid, indol-3-acetic acid methyl ester, tryptamine, tryptophan, jasmonic acid and salicylic acid.

16. The method of claim 1, wherein the tissue of a plastid containing organism is tissue from a crop plant selected from the group consisting of maize, rice, soybean, canola, wheat, cotton, sugar cane, and sugar-beet or tissue from the non crop plants of the genus *Arabidopsis*.

\* \* \* \* \*

UNITED STATES PATENT AND TRADEMARK OFFICE
CERTIFICATE OF CORRECTION

PATENT NO. : 9,465,040 B2
APPLICATION NO. : 14/111369
DATED : October 11, 2016
INVENTOR(S) : Regine Fuchs et al.

Page 1 of 1

It is certified that error appears in the above-identified patent and that said Letters Patent is hereby corrected as shown below:

On the Title Page

At item (75), Line 2, "Henningsdorf" should be -- Hennigsdorf --.

Signed and Sealed this
Thirteenth Day of March, 2018

Andrei Iancu
*Director of the United States Patent and Trademark Office*